US005562690A

United States Patent [19]
Green et al.

[11] Patent Number: 5,562,690
[45] Date of Patent: Oct. 8, 1996

[54] APPARATUS AND METHOD FOR PERFORMING COMPRESSIONAL ANASTOMOSES

[75] Inventors: David T. Green, Westport; Charles R. Sherts, Southport; Keith Ratcliff, Sandy Hook, all of Conn.

[73] Assignee: United States Surgical Corporation, Norwalk, Conn.

[21] Appl. No.: 150,923

[22] Filed: Nov. 12, 1993

[51] Int. Cl.$^6$ ............................................. A61B 17/00
[52] U.S. Cl. ........................ 606/154; 606/151; 673/12
[58] Field of Search ................................ 606/151, 152, 606/153–156, 148, 150; 623/1, 12

[56] References Cited

U.S. PATENT DOCUMENTS

| | | |
|---|---|---|
| 2,453,056 | 11/1948 | Zack. |
| 3,155,095 | 11/1964 | Brown. |
| 3,265,069 | 8/1966 | Healy et al.. |
| 3,316,914 | 5/1967 | Collito. |
| 3,774,615 | 11/1973 | Lim et al.. |
| 3,974,835 | 8/1976 | Hardy, Jr.. |
| 4,055,186 | 10/1977 | Leveen. |
| 4,214,586 | 7/1980 | Mericle. |
| 4,467,804 | 8/1984 | Hardy et al.. |
| 4,552,148 | 11/1985 | Hardy, Jr. et al.. |
| 4,567,891 | 2/1986 | Kanshin et al.. |
| 4,598,712 | 7/1986 | Rebuffat et al.. |
| 4,624,257 | 11/1986 | Berggren et al.. |
| 4,632,435 | 12/1986 | Polyak. |
| 4,667,673 | 5/1987 | Li. |
| 4,681,108 | 7/1987 | Rosati et al.. |
| 4,752,024 | 6/1988 | Green et al.. |
| 4,903,697 | 2/1990 | Resnick et al.. |
| 4,907,591 | 3/1990 | Vasconcellos et al.. |
| 4,931,057 | 6/1990 | Cummings et al.. |
| 4,957,499 | 9/1990 | Lipatov et al.. |
| 4,964,863 | 10/1990 | Kanshin et al.. |
| 4,966,602 | 10/1990 | Rebuffat et al.. |
| 5,282,810 | 2/1994 | Allen et al.. |
| 5,290,298 | 3/1994 | Rebuffat et al.. |

FOREIGN PATENT DOCUMENTS

| | | | |
|---|---|---|---|
| 0517488 | 12/1992 | European Pat. Off.. | |
| 1398843 | 5/1988 | U.S.S.R. | ............................. 606/153 |
| 1537228 | 1/1990 | U.S.S.R.. | |

OTHER PUBLICATIONS

Rebuffat et al., Clinical Application of a New Compression Anastomotic Device for Colorectal Surgery, The American Journal of Surgery, vol. 159, pp. 330–335, Mar. 1990.

Rosati et al., A New Mechanical Device for Circular Compression Anastomosis, Ann. Surg., vol. 207, No. 3, pp. 245–253, Mar. 1988.

*Primary Examiner*—Gary Jackson
*Assistant Examiner*—Jeffrey A. Schmidt

[57] ABSTRACT

A compression device for the anastomosis of a tubular hollow organ, having a first collapsible member movable between an expanded configuration and a collapsed configuration, said first collapsible member having a first end and a second end; a second collapsible member movable between an expanded configuration and a collapsed configuration, said second collapsible member adapted to be joined with said first end of said first collapsible member; and a third collapsible member adapted to be joined with said second end of said second collapsible member; wherein at least one of said first, second or third collapsible members comprises at least one resilient hinge portion disposed thereon which is parallel to the longitudinal axis of said device to facilitate the collapsibility thereof. Also provided are surgical instruments for carrying and placing the compression device components and a device for approximating surgical devices. A method for forming a compression anastomosis, is also provided.

25 Claims, 12 Drawing Sheets

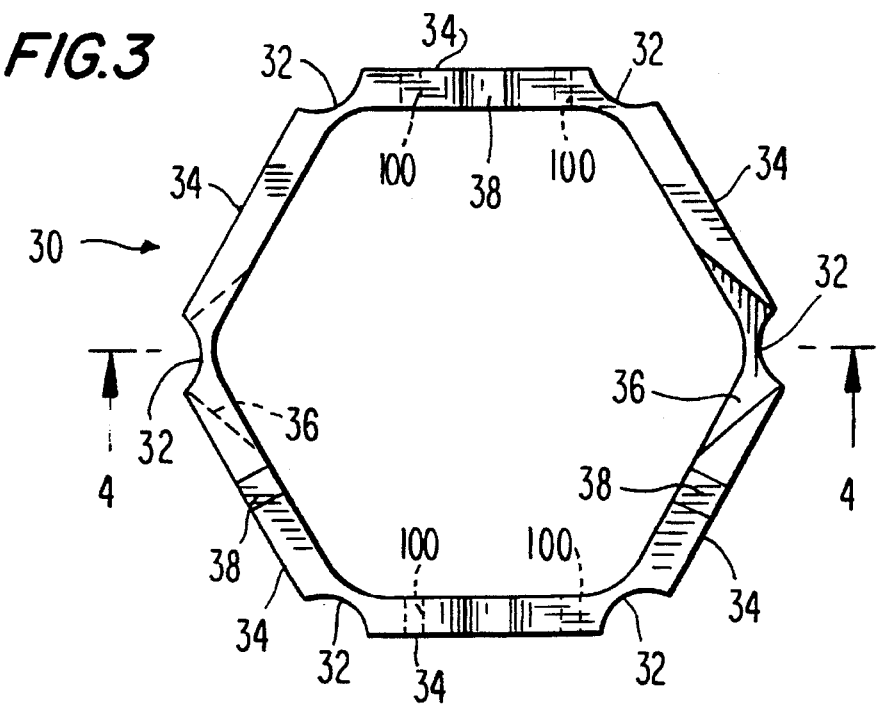
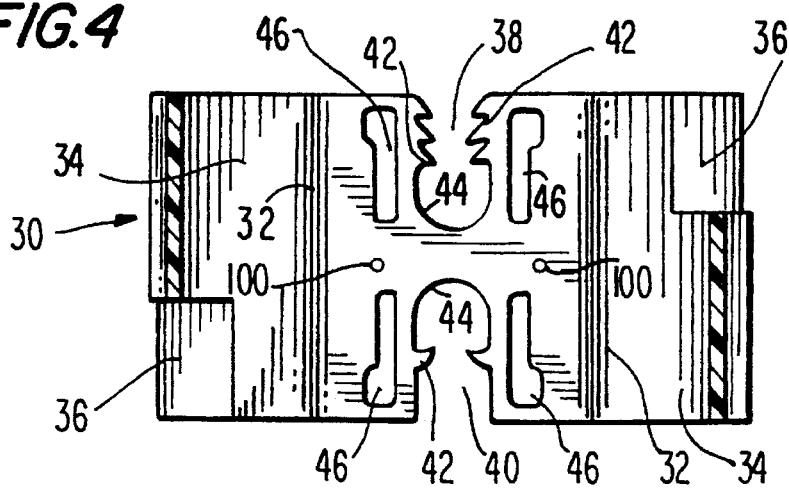
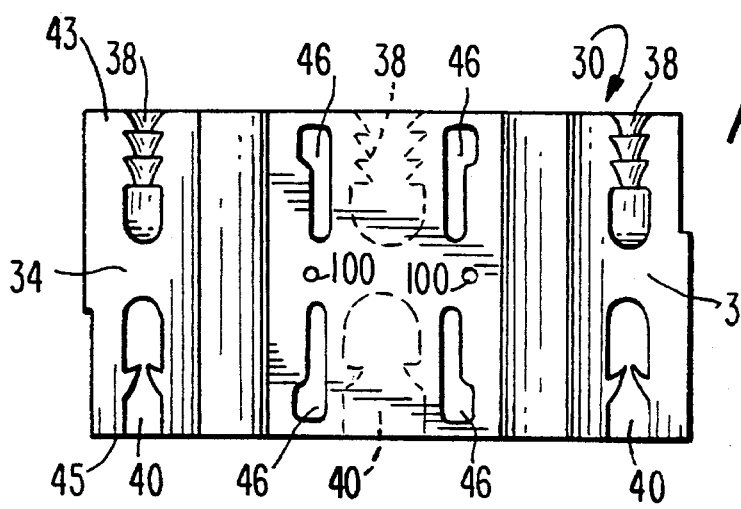

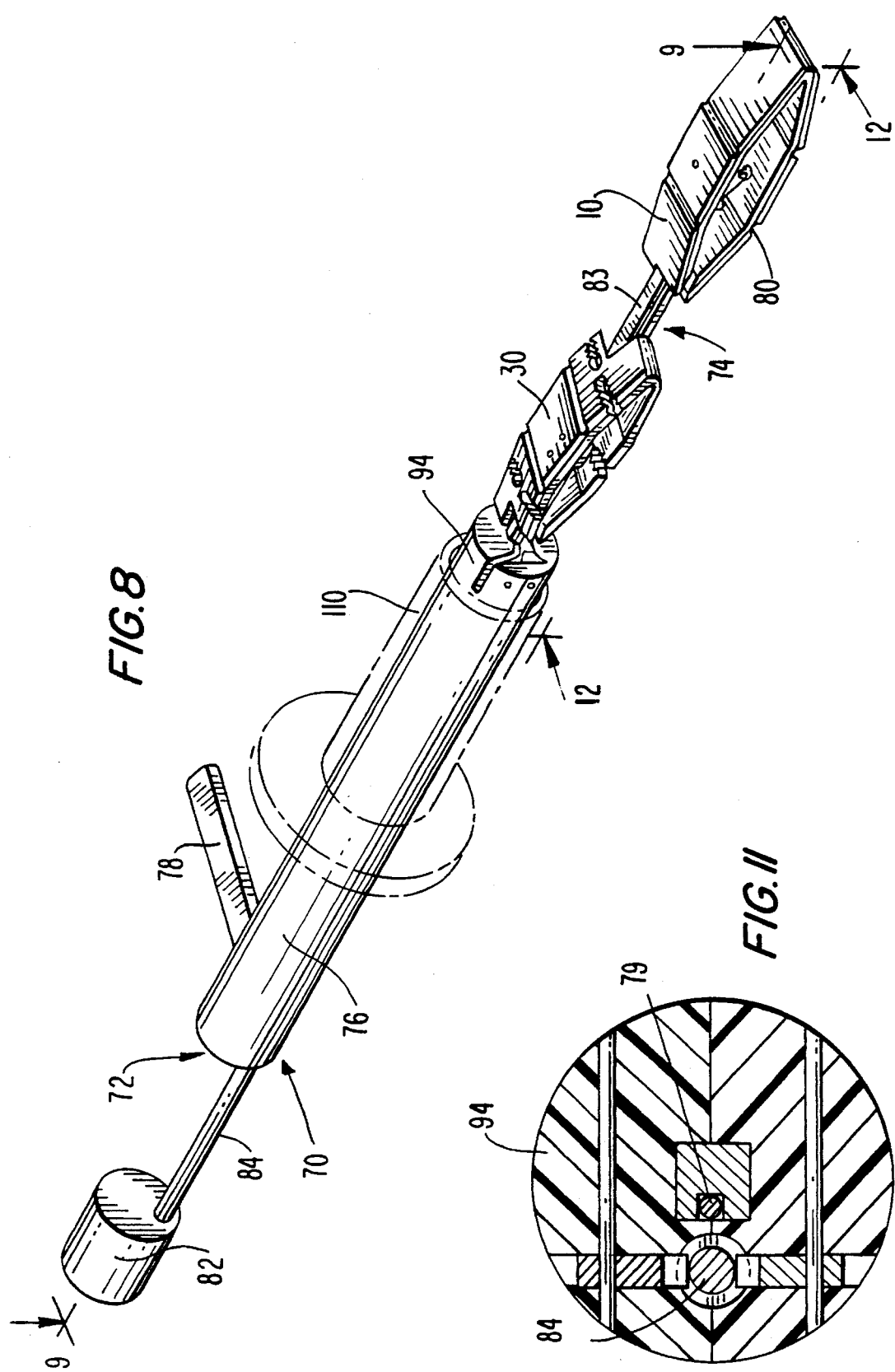

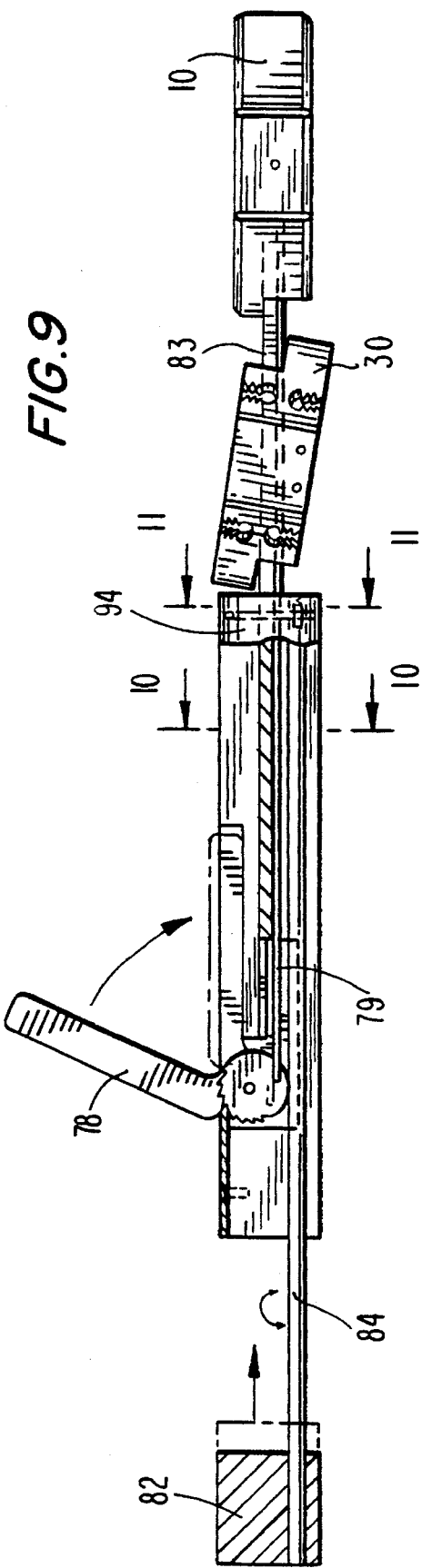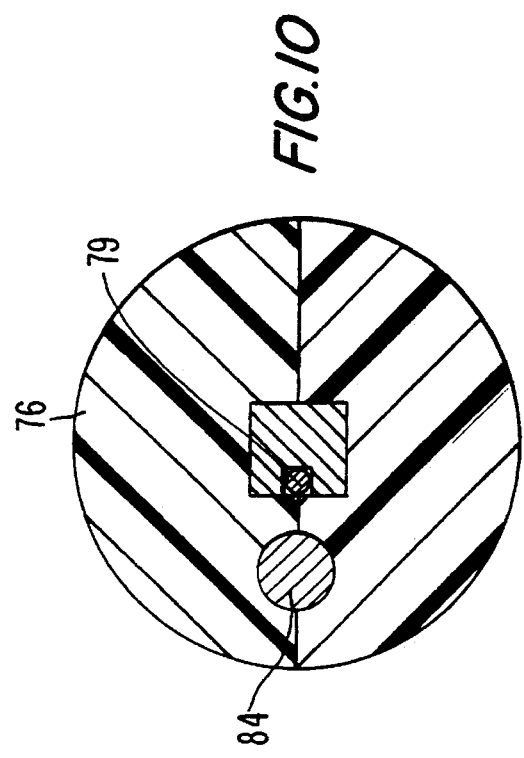

APPARATUS AND METHOD FOR PERFORMING COMPRESSIONAL ANASTOMOSES

BACKGROUND OF THE INVENTION

1. Field of the Invention

The present invention relates to apparatus and method for performing end-to-end compression anastomoses and more particularly, to apparatus and method for performing compression anastomoses endoscopically.

2. Description of the Related Art

Performing anastomoses to connect tissue within the body is well-known in the art. For example, end-to-end anastomoses are commonly performed to join together the ends of tubular organs such as the intestines. Typically, a diseased or blocked portion of the intestine is cut-out and the healthy ends joined together. One method of performing anastomoses involves the use of compression members which compress the ends of the tubular sections to be joined together, thereby allowing a natural anastomosis to occur in the tissue adjacent the compressed tissue. After a period of time, due to necrosis of the compressed edges, the compression devices fall inside the intestine and are then evacuated therefrom during normal excretion of waste. Compression anastomoses have typically been performed by gaining access to the surgical cite either rectally or through open surgery. In the case of the rectally performed procedures, anastomosis is limited to the most distal tracts of the intestine. In the case of open surgery to place compression members, the patient's recovery is lengthened due to the extensive healing required of the incisions made to access the surgical site.

In laparoscopic procedures, surgery is performed in the interior of the abdomen through a small incision; in endoscopic procedures, surgery is performed in any hollow viscus of the body through narrow endoscopic tubes inserted through entrance wounds in the skin. Laparoscopic and endoscopic procedures generally require that any instrumentation inserted into the body be sealed, i.e. provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incisions, thereby requiring that any instruments be used in such procedures be long and narrow while being functionally controllable from the end of the instrument outside the patient's body, i.e. the proximal end. Typically, in laparoscopic and endoscopic procedures, patient recovery time is several days or weeks shorter than that for conventional invasive surgical procedures.

A need presently exits for improved apparatus and methods which facilitate performing anastomoses through small incisions using compression anastomosis devices which fit through cannulas of lesser diameter than the tubular organ to be anastomosed. That is, a need presently exists for improved apparatus and methods capable of performing compressional anastomoses endoscopically or laparoscopically so as to both increase the versatility of the procedure and reduce patient recovery time.

SUMMARY OF THE INVENTION

The present invention provides novel apparatus and method for compression anastomoses.

A compression device is provided for the anastomosis of a tubular hollow organ, comprising a collapsible member movable between an expanded configuration and a collapsed configuration, the collapsible member having a first end and a second end wherein the collapsible member includes at least one resilient hinge disposed thereon which is parallel to the longitudinal axis of the device to facilitate the collapsibility thereof. The collapsible member includes at least three side walls forming a closed construction, the side walls having one resilient hinge disposed between each adjacent side wall.

Alternatively, a compression device for the anastomosis of a tubular hollow organ is provided which comprises a collapsible member movable between an expanded configuration and a collapsed configuration, the collapsible member having a first end and a second end and means disposed thereon for facilitating the collapsing of the collapsible member whereby when the collapsible member is in the expanded configuration, the first and second ends are both open and when the collapsible member is in the collapsed configuration, the first and second ends are both closed.

In another embodiment, the compression anastomosis device comprises a first collapsible member movable between an expanded configuration and a collapsed configuration the first collapsible member having a first end and a second end; a second collapsible member movable between an expanded configuration and a collapsed configuration, the second collapsible member adapted to be joined with the first end of the first collapsible member; and a third collapsible member adapted to be joined with the second end of the second collapsible member; wherein at least one of the first, second or third collapsible members comprises at least one resilient hinge portion disposed thereon which is parallel to the longitudinal axis of the device to facilitate the collapsibility thereof.

In a preferred embodiment, each of the first, second and third collapsible members, respectively, comprises at least one resilient hinge disposed thereon which is parallel to the longitudinal axis of the device to facilitate the collapsibility thereof. The first, second and third collapsible members are configured and dimensioned such that they are insertable in a trocar cannula when the first, second, and third collapsible members are in the collapsed configurations. Further, at least one of the first, second or third collapsible members is made from bioabsorbable materials.

The third collapsible member is adapted to be joined with second collapsible member such that a gap is formed between an end portion of each of the first and second collapsible members when the first, second and third collapsible members are joined. In one preferred embodiment, adjusting means are disposed on at least one of the first, second or third collapsible members, for adjusting the size of the gap formed between the first and second collapsible members. The adjusting means may include first and second engaging portions disposed on the second collapsible member adapted for engaging the first and third collapsible members.

In one embodiment, the first and third collapsible members have a plurality of sidewalls and at least one projecting portion extending from at least one of the sidewalls, the projecting portions being adapted for cooperatively mating with either the first or the second engaging portions of the second collapsible member. Preferably, the first engaging portion includes at least one notched portion formed in a-wall portion of the second engaging portion. The notched portion may have a plurality of individual notches disposed thereon to provide a predetermined number of adjustments when either the first or the second collapsible members is attached to the second engaging portion disposed on the second collapsible member.

To facilitate insertion through a trocar cannula, the first and second collapsible members include means for pivotably engaging a surgical instrument for inserting the first and second collapsible members through the trocar cannula.

A surgical instrument is also provided for carrying and attaching separate components of a compression anastomosis device to the end of tissue of a tubular hollow organ. The instrument comprises an elongated housing having a proximal end and a distal end; a first support member operatively associated with the distal end of the elongated housing, adapted to pivotably support a first compression anastomosis device component; a second support member operatively associated with the distal end of the elongated housing, adapted to pivotably support a second compression anastomosis device component; and an approximating mechanism operatively associated with the first and second support means, the approximating mechanism being operable from the proximal end of the elongated housing and adapted such that movement of the approximating mechanism causes the first and second support members to move relatively toward and away from each other along the longitudinal axis of the instrument. An actuating member may be provided which is operatively connected to the proximal end of the elongated housing, wherein the actuating member can selectively actuate the approximating mechanism such that the approximating mechanism travels a predetermined distance.

A surgical instrument is also provided for approximating surgical devices. The approximating instrument comprises a handle portion disposed at a proximal end of the instrument; an elongated body portion having a proximal end extending from the handle portion and a distal end; and approximating means connected to the distal end of the elongated body portion and operatively associated with the handle portion, for approximating a surgical device inserted therein, the approximating means being movable between a retracted position, such that the instrument is insertable through a trocar cannula, and an extended position, the approximating means being further movable parallel to a longitudinal axis of the elongated body portion between a first position for engaging the surgical device and a second position for approximating the surgical device.

The approximating means preferably includes first and second pairs of finger members, at least one of the first or the second pairs of finger members being longitudinally slidable.

A method for forming a compression anastomosis is provided and comprises the steps of providing a compression device for the anastomosis of hollow organs, the device including at least three collapsible components, wherein at least one of the at least three collapsible components has at least one resilient hinge portion disposed thereon to facilitate the collapsibility thereof, each of the collapsible components having sidewalls defining an opening; providing a surgical instrument adapted for carrying and attaching at least two of the collapsible components to each other and to the end of a tubular tissue section; providing a surgical device for approximating at least two of the collapsible components, which device includes an elongated housing and at least two approximating members operatively attached to the elongated housing, at least one of the at least two approximating members being operable between a first position and a second position; inserting the collapsible members in open ends of tubular tissue sections to be joined using the surgical instrument for carrying and attaching separate components of a compression anastomosis device to the end of a tubular tissue section; and approximating the inserted first and second tubular tissue members using the approximating device such that the first, second and third collapsible members are interlocked together.

Additionally the method may further comprise the step of pivoting at least two of the collapsible components on the surgical instrument for carrying and attaching separate components of a compression anastomosis device prior to the inserting step, such that the at least two collapsible components are positioned substantially transverse to their initial position on the carrying and attaching instrument. The method preferably includes expanding the first second and third collapsible instruments from a collapsed position to an expanded position.

BRIEF DESCRIPTION OF THE DRAWINGS

FIG. 3 is a plan view of the inner collapsible ring of the compression anastomosis device of the present invention;

FIG. 4 is a cross-sectional view taken along section line 4—4 of FIG. 3;

FIG. 5 is a side view of the embodiment of FIG. 3;

FIG. 8 is a perspective view of the ring insertion instrument of the present invention;

FIG. 9 is a horizontal cross-sectional view taken along the section line 9—9 of FIG. 8;

FIG. 10 is a cross-sectional view taken along section line 10—10 of FIG. 9;

FIG. 11 is a cross-sectional view taken along section line 11—11 of FIG. 9;

DETAILED DESCRIPTION OF THE PREFERRED EMBODIMENTS

In general, the overall objective of the method and apparatus is to endoscopically place a collapsible anastomotic compressional ring device to achieve an end-to-end anastomosis without resorting to open surgery or performing the anastomosis by rectal access. The invention includes three main parts: a collapsible ring assembly, a ring insertion instrument and a ring approximation instrument. The following is a short description of the parts of the collapsible ring assembly and the function or overall operation of the instruments used to place and join the rings.

Briefly, the collapsible ring assembly includes three collapsible rings: an inner ring, and two outer rings which are adapted to mate with the inner ring. A ring insertion instrument is utilized to first insert through a trocar cannula, the inner ring and one outer ring and connect the two rings to the end of a tubular tissue section and to themselves. Next, the ring insertion instrument is utilized to insert the second outer ring through the trocar cannula and to connect the second outer ring to the end of another tubular tissue section and to the inner ring so that a compressional anastomosis is formed.

Figure 1:
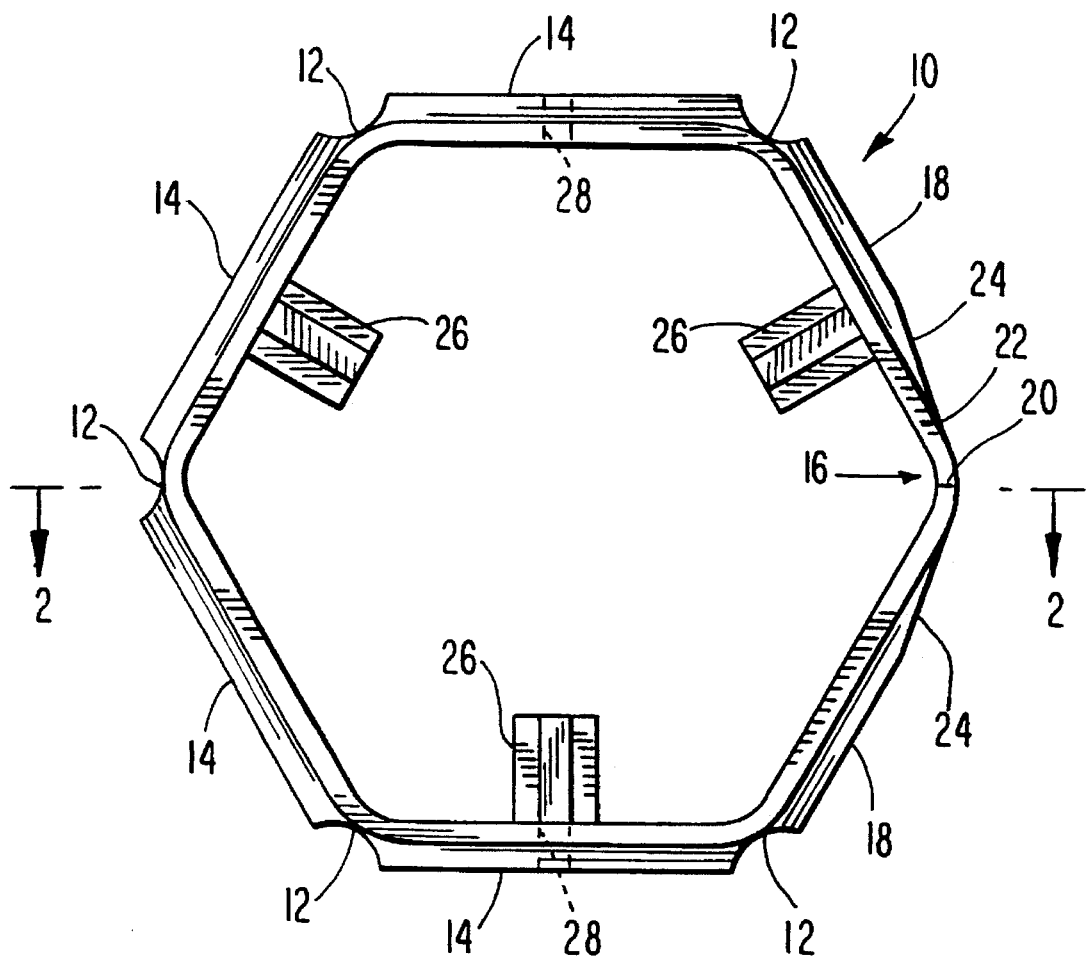
FIG. 1 is a plan view looking up from the bottom of the outer collapsible ring of the compression anastomosis device of the present invention.
Figure 2:
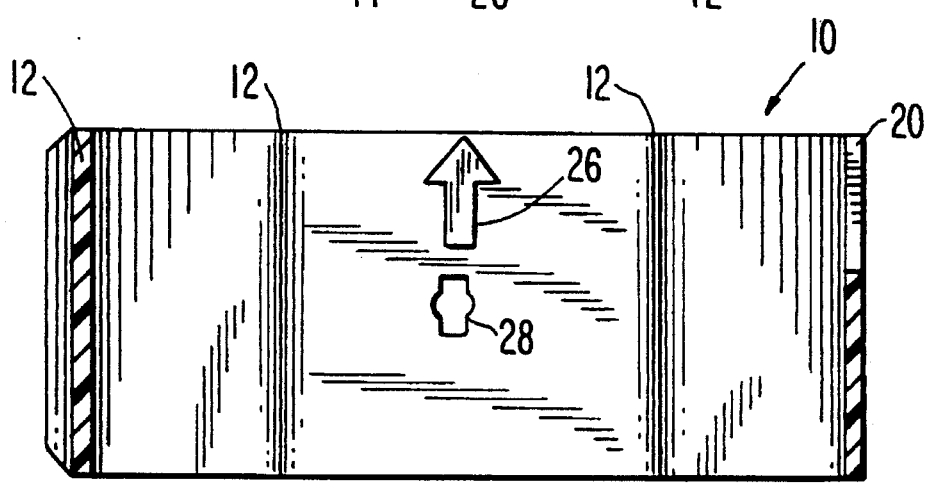
FIG. 2 is a cross-sectional view taken along section line 2—2 of FIG. 1.

One preferred embodiment of the collapsible rings of the present invention will now be described in detail with reference to FIGS. 1–5. FIGS. 1 and 2 illustrate outer ring 10 which is substantially hexagonal shaped. The hexagonal shape is beneficial because it closely approximates a circular ring, while facilitating collapsibility of the ring. As described above, the present invention includes two outer rings which are collapsible. The two outer rings are typically identical and, therefore only one of which will be referred to in this discussion. Preferably, the collapsible rings are made from either partially or totally bioabsorbable materials, such as, e.g., polylactide, polyglycolide, polydioxanone homopolymers, co-polymers or blends thereof.

Outer ring 10 has hinge portions 12 which are formed at the intersections of side walls 14 and hinge portion 16 formed at the intersection of side walls 18. Hinge portions 12 and 16 are referred to as "living hinges" because of their resiliency and structure which is unitary with that of the collapsible ring. Typically the hinge portions are formed from weakening the material of the ring by processes such as heat welding or injection molding. Hinge portions 12 are formed in the shape of an arcuate groove such as, for example, by the removal of material from the thickness of the ring walls or by injection molding of the material. A slit 20 is formed in wall perimeter 22 of hinge portion 16 and extends partially through the material, as best illustrated in FIG. 2. Side walls 18 are preferably tapered along slopes 24 to augment the flexibility of hinge portion 16. In an alternative embodiment more than one hinge portion 16 may be formed on the ring, for example, an equal number of hinge portions 12 and 16 may be formed on ring 10.

Also formed on collapsible outer ring 10 is engaging portions such as raised arrow shaped protrusions 26. Protrusions 26 are preferably formed integrally with outer ring 10, for example, during injection molding, or similar processes. These protrusions 26 mate with recesses in the inner ring as will be described below. It is within the scope of the present invention for protrusions 26 to be formed separately from outer ring 10 and mounted thereon for example by forming a bore hole in the side walls of outer ring 10 and forming a mating extended portion on protrusions 26 which may be friction fitted in the bore hole. Other known mounting methods may also be utilized, such as heat welding, bonding with adhesives, etc.

Additionally, outer ring 10 has a pair of openings 28 formed thereon which are configured receive the manipulation control portions of the ring insertion instrument which will be described in detail in the description of FIGS. 8–16.

Inner ring 30 will now be described in detail with reference to FIGS. 3–5. Inner ring 30 is preferably of a lesser overall diameter than outer rings 10 to allow inner ring 30 to fit within outer rings 10 and to hold a layer of tissue in between the inner and outer rings so that the rings securely hold the tissue therebetween. Inner ring 30, similar to outer ring 10, has hinge portions 32 formed at the intersection of side walls 34. These hinge portions are formed in the same manner as described above for hinge portions 12. In order to facilitate the positioning of inner ring 30 on the ring insertion instrument, to be described later, inner ring 30 is provided with cut-out portions 36. In this configuration, inner ring 30 may be pivoted almost 90° on the ring insertion instrument to enable inner ring 30 to fit down an endoscopic surgical trocar cannula, preferably one such as a 15 mm SURGIPORT®, available from United States Surgical Corporation, Norwalk, Conn.

In order to mate with outer rings 10, inner ring 30 is provided with generally U-shaped cut-out portions 38 formed on surface 43 of one of the side walls 34 and cut-out portions 40 formed on the opposing surface 45 of side wall 34. Notched portions or teeth 42 are formed in cut-out portions 38, 40, as shown, to interlock with the respective projections 26 of outer rings 10 when inserted therein. Preferably, either cut-out portion 38 or 40 have at least three teeth 42 disposed on either side of the cut-out portion. There may be as few as one tooth 42 on either side of cut-out portions 38 or 40, as shown in FIG. 4 for cut-out portion 40.

whatever number of teeth 42 are used, there should be an equal amount on corresponding opposed cut-out portions 38 or 40 in order to balance the mating of inner ring 30 and outer rings 10. That is, each cut-out portion 38 should have the same amount of teeth 42 formed thereon as the remaining cut-out portions 38 and each cut-out portion 40 should have the same number of teeth formed thereon as the remaining cut-out portions 40. However, the number of teeth formed on cut-out portions 38 and 40 does not have to be the same. By providing a number of teeth 42, the relative spacing of a pair of outer rings 10 can be readily adjusted to achieve the optimal spacing between the two outer rings. This is important for the formation of the anastomosis.

In particular, when the ends of the tissue to be joined are abutted against one another, the pressure at which the ends of the tissue are biased against one another is important. Too much pressure can result in the blood supply being reduced too low and causing necrosis to occur before the formation of a complete anastomosis of the surrounding tissue. Too little pressure can result in the tissue not being held in abutment properly so that a complete anastomosis is also not formed. The adjustment provided by having a number of teeth 42 also allows the rings to be adapted for different tissue thickness of different patients. Therefore, a single size ring can be made to fit a wider range of patients than otherwise possible. Production costs are therefore reduced and time is saved during the surgical procedure since the surgeon does not have to remove one set of rings if they are not the proper size. The surgeon merely has to adjust the setting of the relative positioning between the outer rings.

Flexible relief ports 46 are provided adjacent cut-out portions 38 and 40 so that upon insertion of protrusions 26 of outer ring 10, wall 44 may flex to reduce the force necessary to insert outer rings 10 over inner ring 30.

Figure 6:
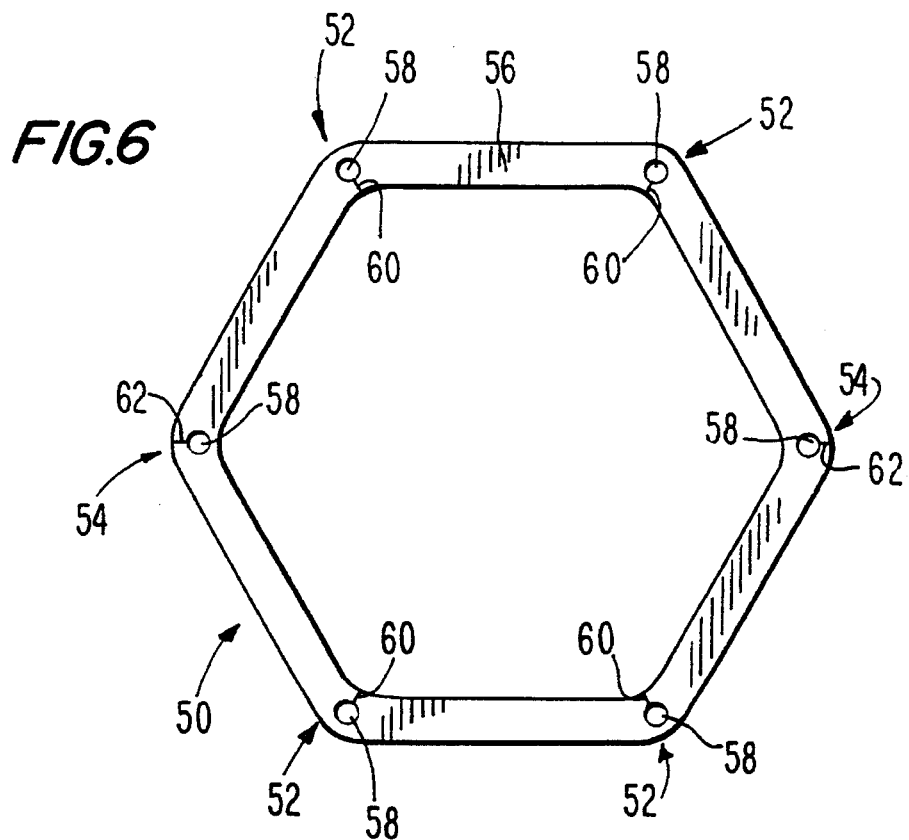
FIG. 6 is a plan view of an alternative embodiment of the hinge design for the collapsible rings of the present invention.
Figure 7:
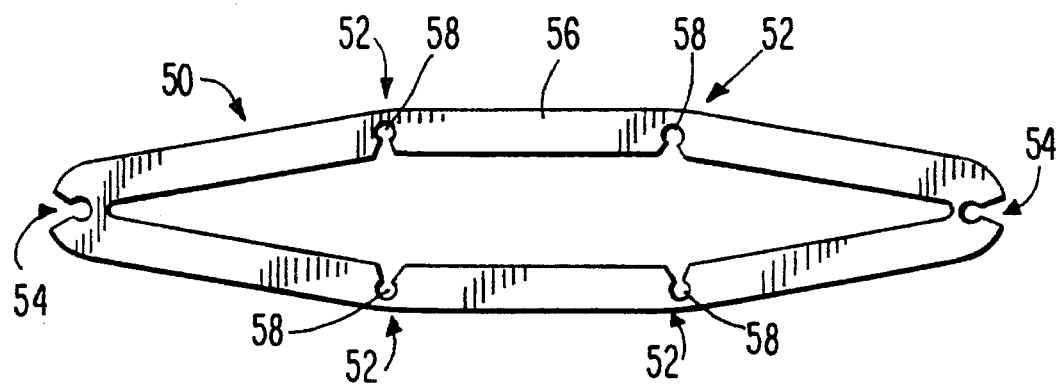
FIG. 7 is a view of the embodiment of FIG. 6 showing the ring in its collapsed state.

FIGS. 6 and 7 show an alternative embodiment of the rings of the present invention. Specifically, a different arrangement of hinged portions is shown. Ring 50 is shown to be representative of the rings of the present invention in general and not to specifically illustrate either an inner or outer ring. Hinge portions 52 and 54 are formed along the inner side of ring wall 56 by first creating bore holes 58 through ring wall 56 at each of the apexes of the hexagonal shaped ring 50. Then, in order to form inwardly opening hinge portions 52, slits 60 are cut into the material of ring wall 56 along the inner side thereof. To form outwardly opening hinge portions 54, slits 62 are cut into the material of ring 50 along the outer side of ring wall 56.

A surgical instrument for carrying and attaching inner ring 30 and outer rings 10, such as elongated ring insertion instrument 70, best shown in FIG. 8, will now be described with reference to FIGS. 8–16. Briefly, ring insertion instrument serves the purpose and function of carrying inner ring 30 and outer rings 10 through a trocar cannula in a collapsed state and then opens the rings to their fully expanded configurations and attaches inner ring 30 to outer rings 10 with the tubular tissue held therebetween in order to form the anastomosis.

Ring insertion instrument 70 has proximal end 72, distal end 74 and elongated endoscopic portion 76 which is adapted for insertion through a trocar cannula as shown in phantom lines in FIG. 8. Except where noted otherwise, the materials utilized in the components of ring insertion instrument 70 generally include such materials as polycarbonate for housing sections and related components, and stainless steel for such components which transmit forces. One preferred polycarbonate material is LEXAN® which is available from General Electric. Other specific preferred materials such as nylon or glass filled nylon (for strength) may also be utilized. However, equivalent alternative materials will readily come to the mind of those skilled in the art.

Referring now to FIGS. 8–11, actuator lever 78 is pivotably mounted adjacent proximal end 72 and is operatively connected to outer ring spreading mechanism 80 which is disposed at the distal-most end of ring insertion instrument 70. When actuator lever is rotated toward the body of ring insertion instrument 70, slidably mounted rod 79 is urged proximally thereby causing outer ring spreading members 81, which are pivotably secured to rigid support member 83, to move radially outward due to movement of the links.

Figure 13:
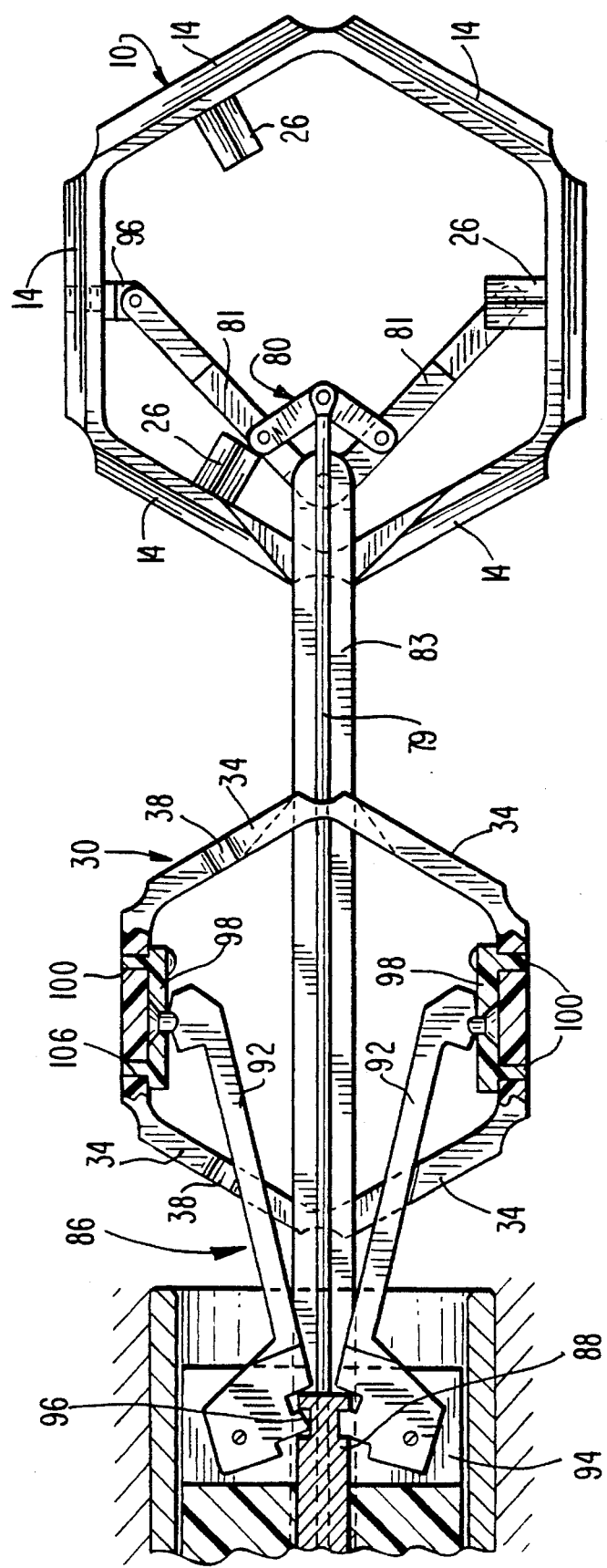
FIG. 13, a view similar to FIG. 12, shows the ring insertion instrument and the collapsible rings of the present invention in their expanded state.
Figure 14:
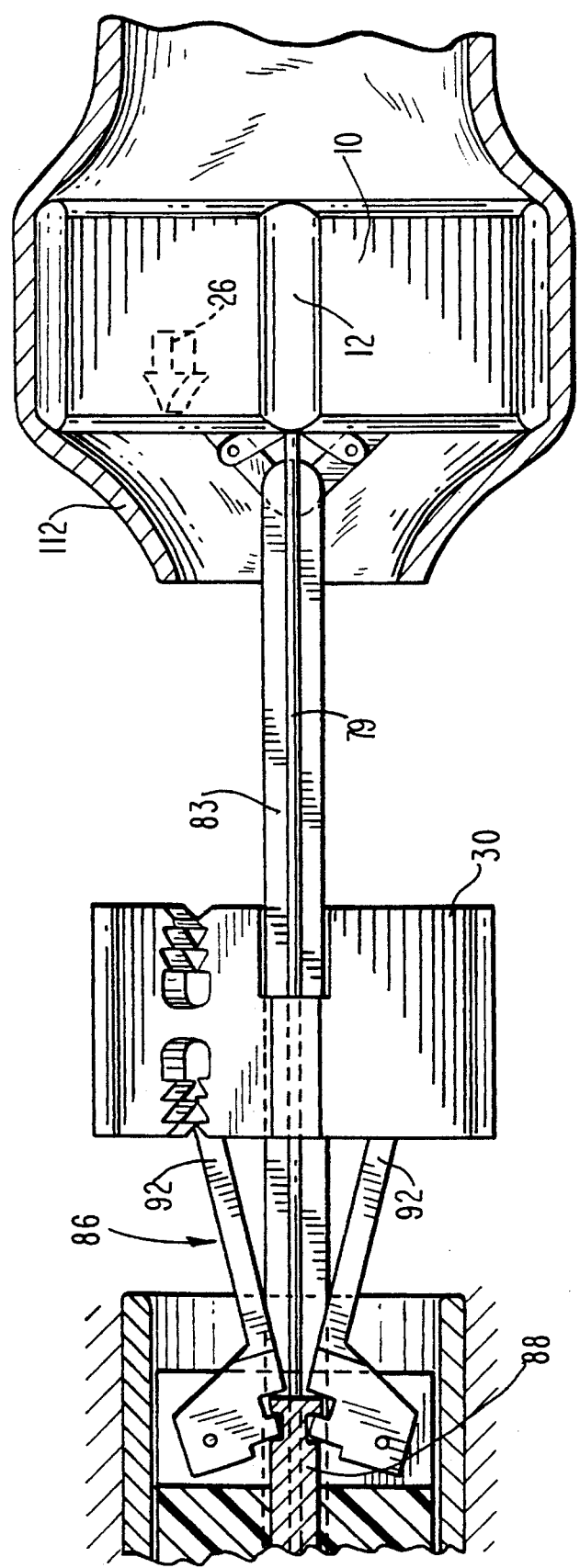
FIG. 14, a view similar to FIG. 13, shows the inner and outer rings pivoted transverse to a longitudinal axis of the ring insertion instrument and the outer ring inserted in one half of the tissue section to be anastomosed.
Figure 15:
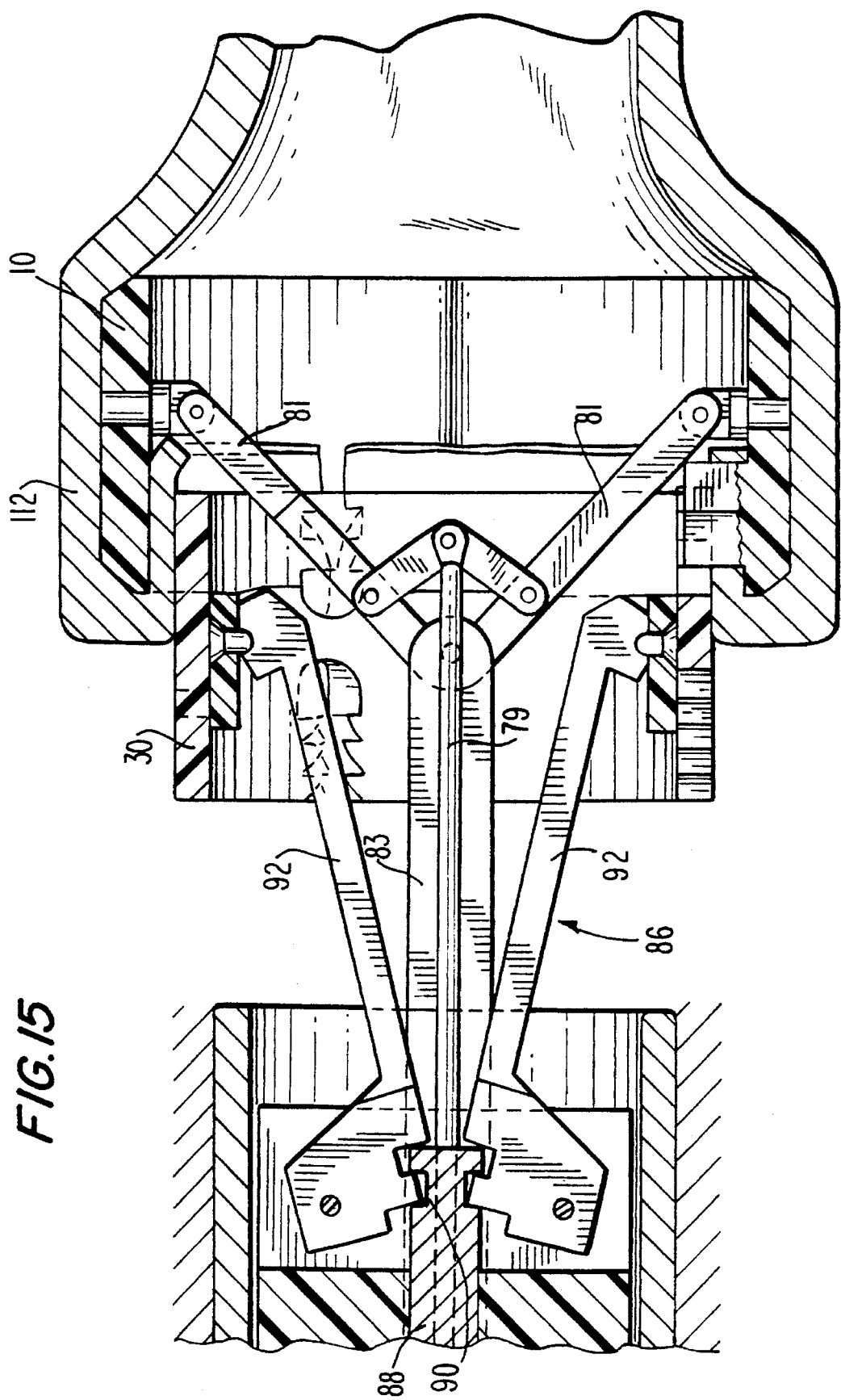
FIG. 15 is an enlarged partial cross-sectional view showing the inner ring inserted in the outer ring.
Figure 16:
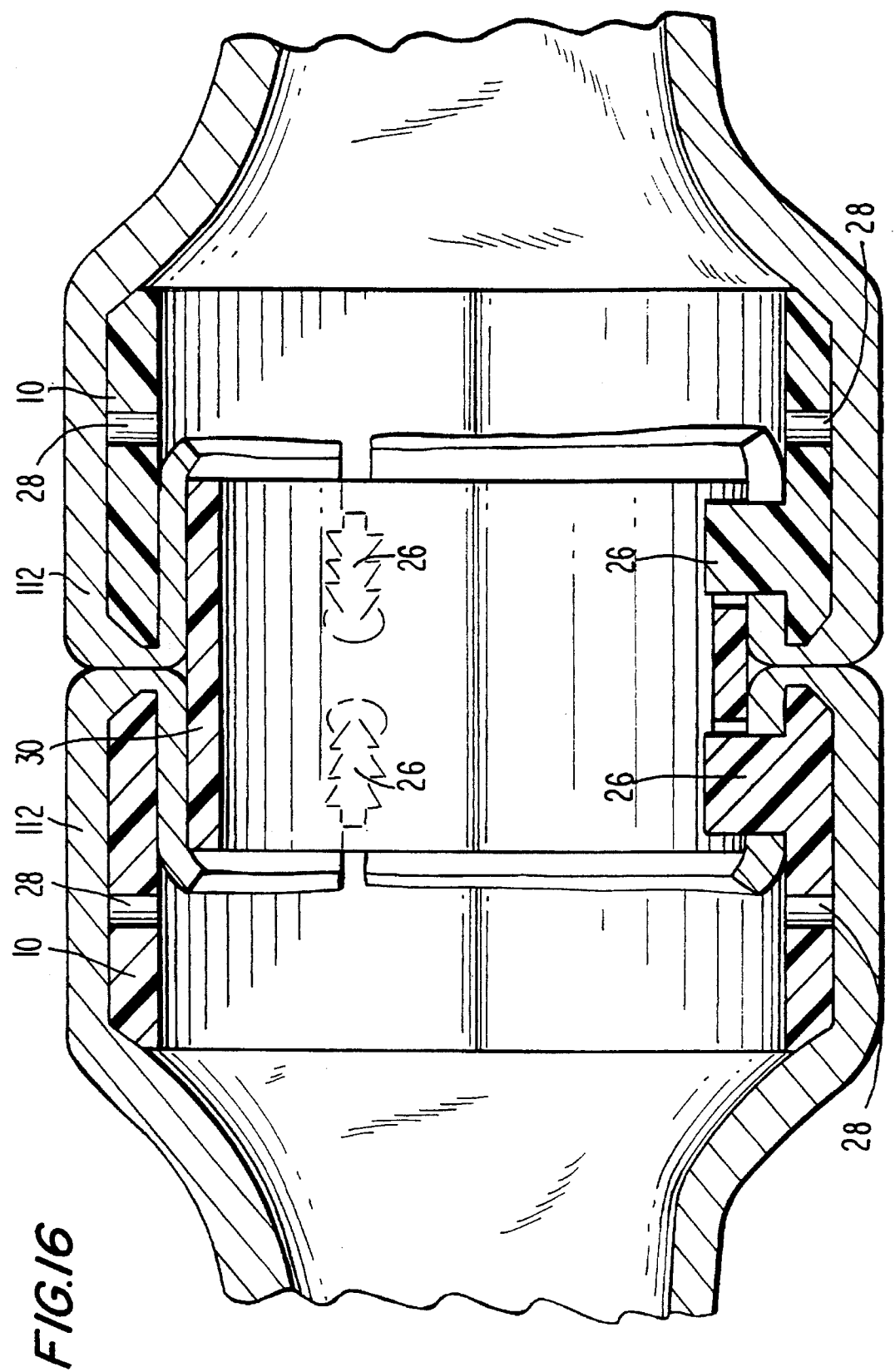
FIG. 16 is an enlarged cross-sectional view showing the completed anastomosis.
Figure 17:
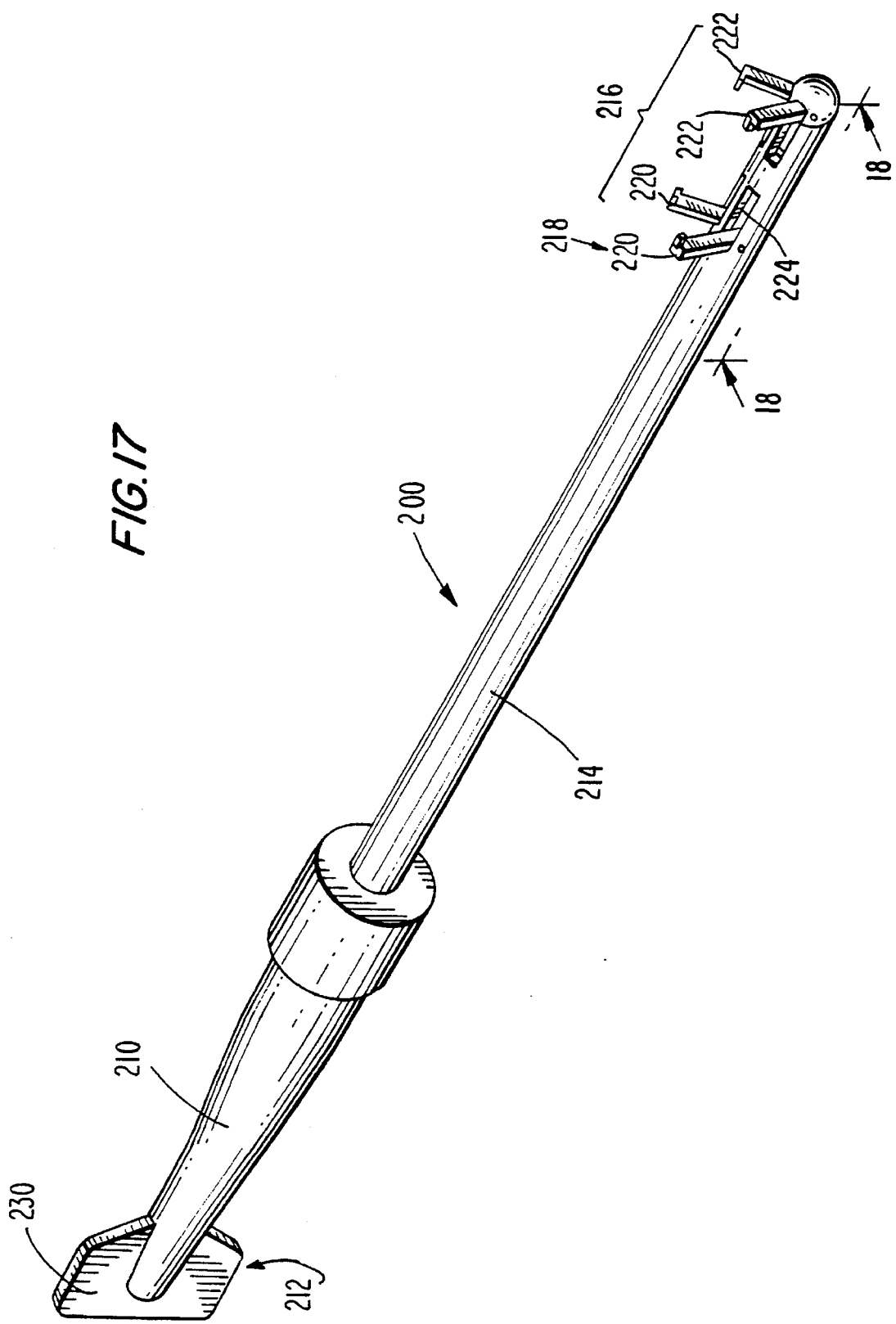
FIG. 17 is a perspective view showing the ring approximation instrument of the present invention.

Knob 82 is disposed adjacent proximal end 72 and is securely mounted to elongated rod 84, which is operatively connected to inner ring spreading mechanism 86 (best illustrated in FIG. 15). Elongated rod 84 is both slidable and rotatable within endoscopic portion 76, as it serves dual functions. Referring to FIGS. 13–15, the first function of elongated rod 84 is achieved by elongated rod 84 being threadably connected to head 88 by an internal threading (not shown). Head 88 is preferably cylindrical and has annular groove 90 formed near the distal end thereof. Ring spreading members 92 are pivotably mounted on slidable end portion 94 of ring insertion instrument 70 in cooperation with annular groove 90 such that rotation of knob 82 in either a clockwise or counter clockwise direction depending on the orientation of the threading, causes head 88 to advance thereby urging ring spreading members 92 radially outward.

The second function of elongated rod 84, urging inner ring 30 to mate with outer ring 10, is achieved by sliding knob 82 distally. Once ring spreading members 92 have reached the limit of their pivoting motion as defined by the size of the ring, i.e., once the ring is fully expanded, ring spreading members are prevented from further spreading due to the resistance provided by the ring itself. Thus, inner ring 10 is securely held by spreading members 92. Pushing distally on knob 82 will cause end portion 94 of ring insertion instrument to slide distally away from the main body of the instrument toward outer ring spreading mechanism 80, thereby carrying ring spreading members 92 with it.

Figure 12:
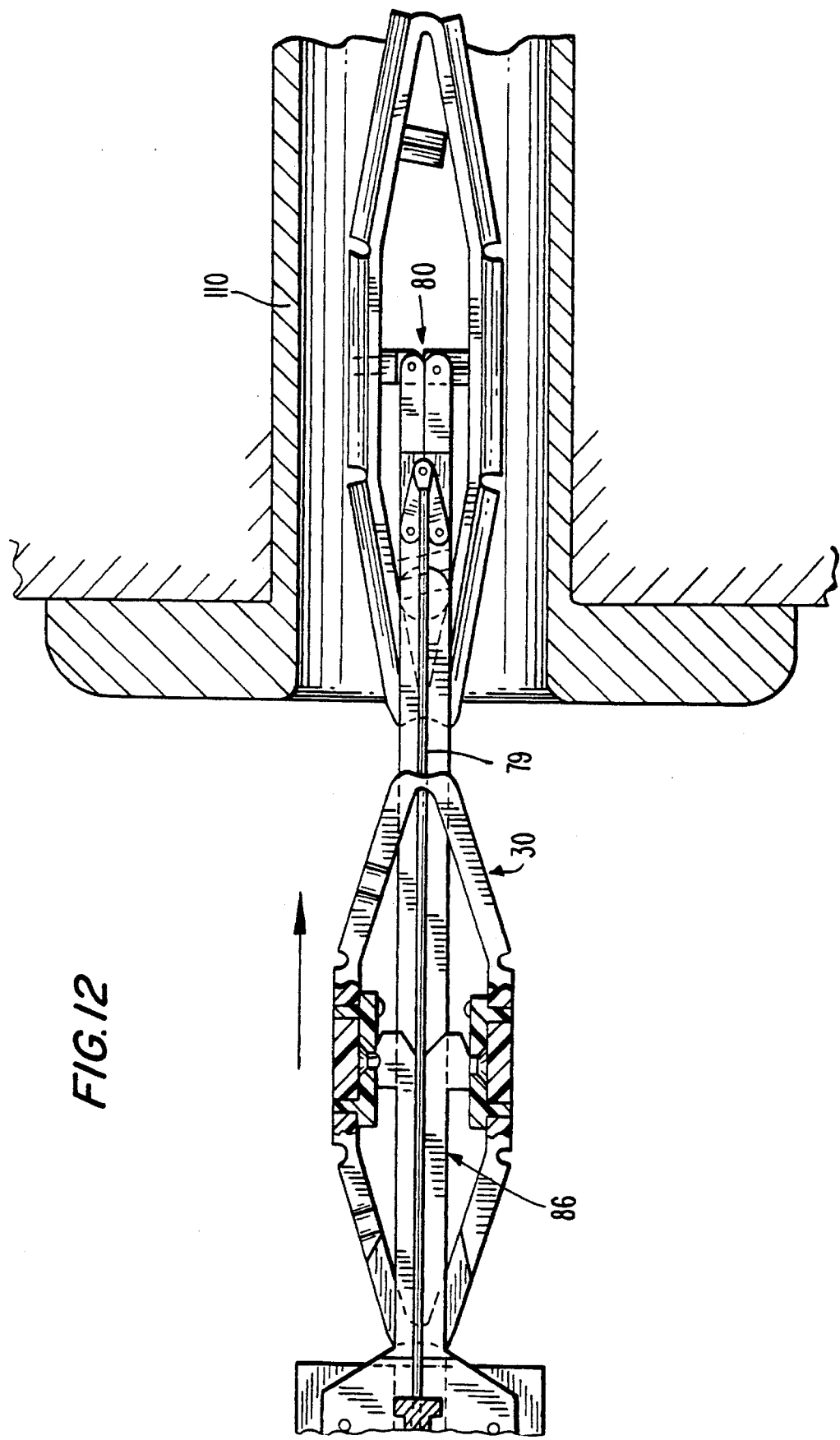
FIG. 12 is a partial view of the distal end of the ring insertion instrument of the present invention as the instrument is inserted through a trocar cannula.

In use, prior to insertion of ring insertion instrument 70, inner ring 30 and an outer ring 10 are mounted on ring insertion instrument 70. Outer ring 10 is mounted on outer ring spreading mechanism 80 by way of pivotable extending portions 96 mounted on outer ring spreading members 81 fitting in openings 28 formed in opposing side walls 18. Inner ring 30 is mounted on inner ring spreading mechanism 86 by way of pivotable brackets 98, which are mounted on inner ring spreading members 92, fitting in openings 100 formed in opposing side walls 34. Ring insertion instrument 70 together with the loaded inner ring 30 and outer ring 10 are inserted through the previously placed trocar cannula 110 as shown in FIGS. 8 and 12.

Once inserted through trocar cannula 110, inner and outer rings 30 and 10, respectively are pivoted, preferably by a grasping instrument (not shown), to be perpendicular to the central longitudinal axis of ring insertion instrument 70. Inner and outer ring spreading mechanisms 86 and 80, respectively, are actuated, as previously described, to effect expansion of inner ring 30 and outer ring 10, as shown in FIG. 13. Tissue 112 of one half of the tubular organ section to be anastomosed is pulled over outer ring 10, as shown in FIG. 14, by known endoscopic instruments, such as graspers or forceps. Knob 82 is pushed in a distal direction to urge end portion 94 distally towards outer ring spreading mechanism 80, thereby urging inner ring 30 to mate with outer ring 10. Specifically, protrusions 26 of outer ring 10 spread teeth 42 of cut-out portions 38 on inner ring 30 and engage them thereby joining inner ring 30 and outer ring 10 with tissue 112 held therebetween, as best shown in FIG. 15.

To place the second outer ring 10, ring insertion instrument is removed by reversing the steps used to spread ring spreading mechanisms 80 and 86, i.e., pivoting lever 78 and rotating knob 82 in the opposite direction, and pulling ring insertion instrument 70 out from within trocar cannula 110. The second outer ring 10 is placed on outer ring spreading mechanism 80 and the instrument reinserted through trocar cannula 110. The second outer ring 10 is then pivoted to a perpendicular position and lever 78 is pivoted to move outer ring 10 to its open position. The second end of tissue 112 to be anastomosed is pulled over the second outer ring 10 and folded inward. The second outer ring 10 is then approximated with inner ring 30 by the instruments described below so that it mates with the inner ring via the cooperation between teeth 42 of cut-out portions 40 on inner ring 30 and protrusions 26 on outer ring 10 and engage them thereby joining inner ring 30 and outer ring 10 with tissue 112 held therebetween in the same manner as the first outer ring 10 mates with inner ring 30.

Preferably the joining of the second outer ring 10 with the previously joined inner ring 30 and first outer ring 10 is effected by a specially developed instrument such as ring approximation instrument 200. Ring approximation instrument includes handle 210 disposed at proximal end 212, an elongated body portion 214 configured and dimensioned to be readily inserted through a trocar cannula such as trocar cannula 110 and ring approximation mechanism 216 disposed at distal end 218.

Figure 18:
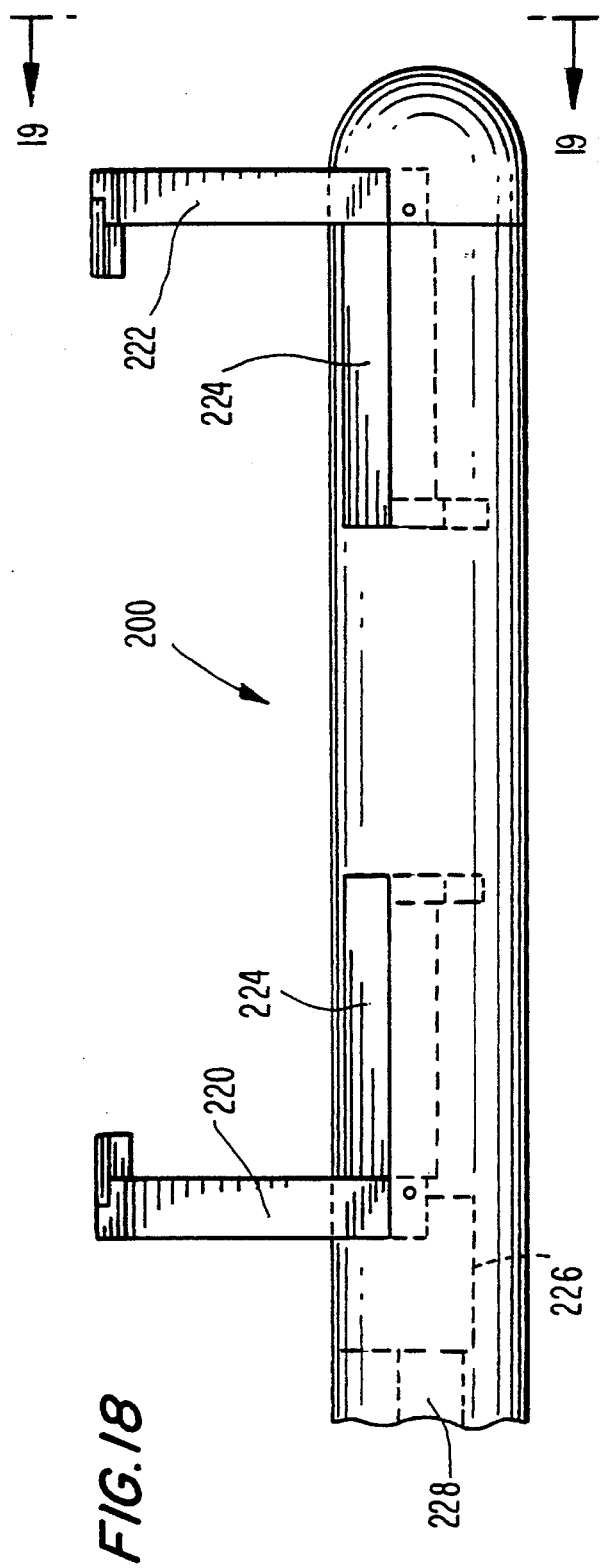
FIG. 18 is an enlarged partial side view of the distal end of the ring approximation instrument of FIG. 17.
Figure 19:
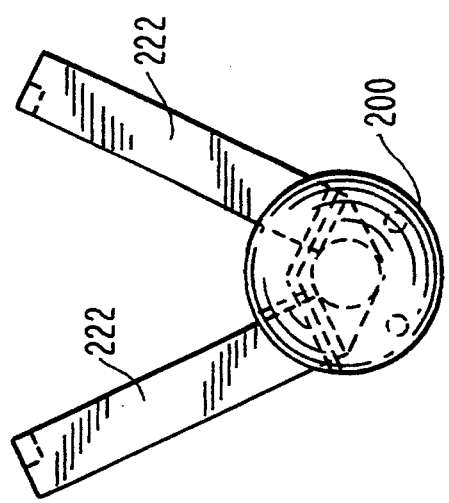
FIG. 19 is an end view taken along line 19—19 of FIG. 18.

Ring approximation mechanism is made up of pivotably retractable arms 220 and 222. Recesses 224 are formed in elongated body portion 214 and are configured and dimensioned to receive pivotable arms 220 and 222 so that the arms are substantially flush with elongated body portion 214 when the arms are in their retracted state as shown in phantom lines in FIG. 18. Arms 220 are mounted to slidable block 226 which is preferably threadably mounted to elongated rod 228, both shown in phantom lines in FIG. 18. Elongated rod 228 is rigidly secured to rotatable handle 210. In order to provide easier rotation, handle 210 is provided with wing portion 230. Depending on the orientation of the threading connection between slidable block 226 and elongated rod 228, either clockwise or counter clockwise rotation of handle 210 will advance slidable block 226 distally, thereby moving arms 220 distally.

In use, the partially approximated inner and outer ring assembly described above is inserted on ring approximation instrument 200 so that outer rings 10 are situated between arms 220 and 222. Handle 210 is then rotated in the appropriate direction to approximate arms 220 and 222, until the desired approximation of the adjustable outer-inner-outer ring assembly is reached.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A compression device for the anastomosis of a tubular hollow organ, comprising a collapsible member movable between an expanded configuration and a collapsed configuration, said collapsible member having a first end and a second end wherein said collapsible member includes at least one resilient hinge disposed thereon which is parallel to a longitudinal axis of said device to facilitate the collapsibility thereof, said at least one resilient hinge having a greater degree of flexibility than sections of said collapsible member adjoined by said at least one resilient hinge such that said collapsible member remains intact upon collapse thereof.

2. A compression device for the anastomosis of a tubular hollow organ, according to claim 1 wherein said collapsible member further includes at least three side walls forming a closed construction, said side walls having one said resilient unitary hinge disposed between each adjacent side wall.

3. A compression device for the anastomosis of a tubular hollow organ, comprising a collapsible member movable between an expanded configuration and a collapsed configuration, said collapsible member having a first end and a second end and at least one hinge having a greater degree of flexibility than sections of said collapsible member adjoined by said at least one resilient hinge for facilitating the collapsing of said collapsible member whereby when said collapsible member is in said expanded configuration, said first and second ends are both open and when said collapsible member is in said collapsed configuration, said first and second ends are both substantially closed.

4. A compression device for the anastomosis of a tubular hollow organ, comprising:

(a) a first collapsible member movable between an expanded configuration and a collapsed configuration, said first collapsible member having a first end and a second end;

(b) a second collapsible member movable between an expanded configuration and a collapsed configuration, said second collapsible member having a first end and a second end and structure for joining said first end of said second collapsible member with said second end of said first collapsible member; and (c) a third collapsible member having structure for joining with said second end of said second collapsible member;

wherein at least one of said first, second or third collapsible members comprises at least one resilient hinge portion disposed thereon which is parallel to a longitudinal axis of said device to facilitate the collapsibility thereof such that said at least one of said first, second or third collapsible members remains intact upon collapse thereof.

5. A compression device for the anastomosis of a tubular hollow organ, according to claim 4, wherein each of said first, second and third collapsible members, respectively comprises at least one resilient hinge disposed thereon which is parallel to the longitudinal axis of said device to facilitate the collapsibility thereof.

6. A compression device for the anastomosis of hollow organs according to claim 4, wherein said first, second and third collapsible members are configured and dimensioned such that they are insertable in a trocar cannula when said first, second, and third collapsible members are in said collapsed configurations.

7. A compression device for the anastomosis of hollow organs according to claim 6, wherein said first and second collapsible members include means for pivotably engaging a surgical instrument for inserting said first and second collapsible members through said trocar cannula.

8. A compression device for the anastomosis of hollow organs according to claim 4, wherein at least one of said first, second or third collapsible members is made from bioabsorbable materials.

9. A compression device for the anastomosis of hollow organs according to claim 4, wherein said first, second, and third collapsible members are made from partially bioabsorbable materials.

10. A compression device for the anastomosis of hollow organs according to claim 4, wherein said first, second, and third collapsible members are made from totally bioabsorbable materials.

11. A compression device for the anastomosis of hollow organs according to claim 4, wherein each of said first, second and third collapsible members, respectively, comprises a plurality of resilient hinge portions disposed thereon to facilitate the collapsibility thereof.

12. A compression device for the anastomosis of hollow organs according to claim 11, wherein at least one of said resilient hinge portions is disposed along an inner surface of at least one of said first, second or third collapsible members.

13. A compression device for the anastomosis of hollow organs according to claim 11, wherein at least one of said resilient hinge portions is disposed along an outer surface of at least one of said first, second or third collapsible members.

14. A compression device for the anastomosis of a tubular hollow organ, according to claim 4, wherein a gap is formed between an end portion of each of said first and second collapsible members when said first, second and third collapsible members are joined.

15. A compression device for the anastomosis of a tubular hollow organ, according to claim 14, further comprising adjusting means disposed on at least one of said first, second or third collapsible members, for adjusting the size of said gap formed between said first and second collapsible members.

16. A compression device for the anastomosis of hollow organs according to claim 15, wherein said adjusting means includes first and second engaging portions disposed on said second collapsible member adapted for engaging said first and third collapsible members.

17. A compression device for the anastomosis of hollow organs according to claim 16, wherein each said first and third collapsible members have a plurality of sidewalls and at least one projecting portion extending from at least one of said sidewalls, said projecting portions being adapted for cooperatively mating with said either said first or said second engaging portions of said second collapsible member.

18. A compression device for the anastomosis of hollow organs according to claim 16, wherein said first engaging portion includes at least one notched portion formed in a wall portion of said second engaging portion.

19. A compression device for the anastomosis of hollow organs according to claim 18, wherein said at least one notched portion has a plurality of individual notches disposed thereon to provide a predetermined number of adjustments when either said first or said second collapsible members is attached to said second engaging portion disposed on said second collapsible member.

20. A method for forming a compression anastomosis, comprising the steps of:
(a) providing a compression device for the anastomosis of hollow organs, the device including at least three collapsible components, wherein at least one of said at least three collapsible components has at least one resilient hinge portion disposed thereon to facilitate the collapsibility thereof, each of said collapsible components having sidewalls defining an opening;
(b) providing a surgical instrument adapted for carrying and attaching at least two of said collapsible components to each other and to the end of a tubular tissue section;
(c) providing a surgical device for approximating at least two of said collapsible components, which device includes an elongated housing and at least two approximating members operatively attached to said elongated housing, at least one of said at least two approximating members being operable between a first position and a second position;
(d) inserting said collapsible members in open ends of tubular tissue sections to be joined using said surgical instrument for carrying and attaching separate components of a compression anastomosis device to the end of a tubular tissue section; and
(e) approximating said inserted first and second tubular tissue members using said approximating device such that said first, second and third collapsible members are interlocked together.

21. A method for forming a compression anastomosis, according to claim 20, further comprising the step of:
pivoting at least two of said collapsible components on said surgical instrument for carrying and attaching separate components of a compression anastomosis device prior to step (e), such that said at least two collapsible components are positioned substantially transverse to their initial position on said carrying and attaching instrument.

22. A method for forming a compression anastomosis, according to claim 21, further comprising the step of:
expanding said first second and third collapsible instruments from a collapsed position to an expanded position prior to step (d).

23. A compression device for the anastomosis of a tubular hollow organ, comprising:
(a) a first collapsible member movable between an expanded configuration and a collapsed configuration, said first collapsible member having a first end and a second end;
(b) a second collapsible member movable between an expanded configuration and a collapsed configuration, said second collapsible member adapted to be joined with said second end of said first collapsible member; and
(c) a third collapsible member adapted to be joined with said second end of said second collapsible member;
wherein at least one of said first, second or third collapsible members comprises at least one resilient hinge portion disposed thereon which is parallel to the longitudinal axis of said device to facilitate the collapsibility thereof and wherein said first, second and third collapsible members are configured and dimensioned such that they are insertable in a trocar cannula when said first, second, and third collapsible members are in said collapsed configurations.

24. A compression device for the anastomosis of a tubular hollow organ, comprising:
(a) a first collapsible member movable between an expanded configuration and a collapsed configuration, said first collapsible member having a first end and a second end;
(b) a second collapsible member movable between an expanded configuration and a collapsed configuration, said second collapsible member adapted to be joined with said second end of said first collapsible member;
(c) a third collapsible member adapted to be joined with said second end of said second collapsible member; and
(d) adjusting means disposed on at least one of said first, second or third collapsible members, for adjusting the size of said gap formed between said first and second collapsible members;
wherein at least one of said first, second or third collapsible members comprises at least one resilient hinge portion disposed thereon which is parallel to the longitudinal axis of said device to facilitate the collapsibility thereof.

25. A compression device for the anastomosis of a tubular hollow organ, comprising a collapsible member movable between an expanded configuration and a collapsed configuration, said collapsible member having a first end and a second end wherein said collapsible member includes at least one resilient hinge disposed thereon having a greater degree of flexibility than sections of said collapsible member adjoined by said at least one resilient hinge and such that said collapsible member remains intact upon collapse thereof.

* * * * *